US007182761B2

United States Patent
Garabedian et al.

(10) Patent No.: US 7,182,761 B2
(45) Date of Patent: Feb. 27, 2007

(54) ABLATION PROBE WITH TEMPERATURE SENSITIVE ELECTRODE ARRAY

(75) Inventors: Robert J. Garabedian, Mountain View, CA (US); Amy C. Kelly, San Francisco, CA (US); Steven K. Landreville, Mountain View, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 330 days.

(21) Appl. No.: 10/734,648

(22) Filed: Dec. 11, 2003

(65) Prior Publication Data

US 2005/0131508 A1 Jun. 16, 2005

(51) Int. Cl.
*A61B 18/14* (2006.01)
(52) U.S. Cl. .......................................... 606/41; 606/47
(58) Field of Classification Search .................. 606/41, 606/47–50
See application file for complete search history.

(56) References Cited

U.S. PATENT DOCUMENTS

| 5,327,889 | A |   | 7/1994  | Imran          |        |
|-----------|---|---|---------|----------------|--------|
| 5,827,276 | A | * | 10/1998 | LeVeen et al.  | 606/41 |
| 5,855,576 | A |   | 1/1999  | LeVeen et al.  |        |
| 6,063,082 | A | * | 5/2000  | DeVore et al.  | 606/45 |
| 6,090,105 | A | * | 7/2000  | Zepeda et al.  | 606/41 |

(Continued)

FOREIGN PATENT DOCUMENTS

| WO | WO 99/25260 A | 5/1999 |
|----|---------------|--------|
| WO | WO 99/44524 A | 9/1999 |
| WO | WO 02/054941 A | 7/2002 |

OTHER PUBLICATIONS

PCT International Search Report for PCT/US2004/040775, Applicant: Scimed Life Systems, Inc., Forms PCT/ISA/210 and 220, dated Apr. 15, 2005 (9 pages).
PCT Written Opinion of the International Search Authority for PCT/US2004/040775, Applicant: Scimed Life Systems, Inc., Form PCT/ISA/237, dated Apr. 15, 2005 (5 pages).

*Primary Examiner*—Michael Peffley
*Assistant Examiner*—Alex Toy
(74) *Attorney, Agent, or Firm*—Vista IP Law Group LLP

(57) ABSTRACT

A medical probe assembly and method are provided for ablating tissue. The probe assembly comprises an elongated shaft and an electrode array mechanically coupled to the distal end of the shaft. The electrode array is configured to assume an outwardly curved shape, when exposed to a first temperature, and assume a pointed tip when exposed to a second temperature less than the first temperature. The first temperature is preferably greater than body temperature, e.g., equal to the tissue ablation temperature, and the second temperature is preferably less than a tissue ablation temperature, e.g., body temperature. In this manner, the pointed tip assumed by the electrode array facilitates introduction of the probe assembly through the tissue prior to the ablation process, while the outwardly curved shape assumed by the electrode array facilitates deployment of the electrode array within the tissue during the ablation process. The exposed needle electrodes also facilitate the visualization of the probe assembly under fluoroscopy. The probe assembly comprises an optional deployment member, which is configured to linearly expand when exposed to a third temperature, thereby displacing the electrode array.

34 Claims, 4 Drawing Sheets

U.S. PATENT DOCUMENTS

| | | |
|---|---|---|
| 6,221,071 B1 * | 4/2001 | Sherry et al. .................. 606/41 |
| 6,379,353 B1 | 4/2002 | Nichols |
| 6,575,967 B1 * | 6/2003 | Leveen et al. ................ 606/41 |
| 6,780,177 B2 * | 8/2004 | Shafirstein et al. ........... 606/28 |
| 6,905,480 B2 * | 6/2005 | McGuckin et al. .... 604/164.01 |
| 2001/0031963 A1 * | 10/2001 | Sharkey et al. ............... 606/41 |

* cited by examiner

ABLATION PROBE WITH TEMPERATURE SENSITIVE ELECTRODE ARRAY

FIELD OF INVENTION

The invention relates generally to the structure and use of radio frequency (RF) electrosurgical probes for the treatment of tissue, and more particularly, to electrosurgical probes having multiple tissue-penetrating electrodes that are deployed in an array to treat large volumes of tissue.

BACKGROUND

The delivery of radio frequency (RF) energy to target regions within solid tissue is known for a variety of purposes of particular interest to the present invention. In one particular application, RF energy may be delivered to diseased regions (e.g., tumors) for the purpose of ablating predictable volumes of tissue with minimal patient trauma. RF ablation of tumors is currently performed using one of two core technologies.

The first technology uses a single needle electrode, which when attached to a RF generator, emits RF energy from the exposed, uninsulated portion of the electrode. This energy translates into ion agitation, which is converted into heat and induces cellular death via coagulation necrosis. In theory, RF ablation can be used to sculpt precisely the volume of necrosis to match the extent of the tumor. By varying the power output and the type of electrical waveform, it is theoretically possible to control the extent of heating, and thus, the resulting ablation. The diameter of tissue coagulation from a single electrode, however, is limited by heat dispersion. As a result, multiple probe insertions have been required to treat all but the smallest lesions. This considerably increases treatment duration and requires significant skill for meticulous precision of probe placement.

The second technology utilizes multiple needle electrodes, which have been designed for the treatment and necrosis of tumors in the liver and other solid tissues. U.S. Pat. No. 6,379,353 disclose such a probe. The ablation probe disclosed in U.S. Pat. No. 6,379,353, referred to as the LeVeen Needle Electrode, comprises a cannula having a needle electrode array, which is reciprocatably mounted within the cannula to alternately deploy the electrode array from the cannula and retract electrode array within the cannula. The individual electrodes within the array have spring memory, so that they assume a radially outward, arcuate configuration as they are deployed from the cannula. In general, a multiple electrode array creates a larger lesion than that created by a needle electrode.

Prior to deploying the electrode array, the distal tip of the cannula must first be properly positioned at the ablation site—typically using fluoroscopy. Once the correct position is obtained, the electrode array can be deployed from the cannula, and RF ablation can commence. Due to the inability to accurately image the tip of the cannula, however, site targeting is, at times, difficult using the LeVeen Needle Electrode. In addition, the LeVeen Needle Electrode has an open cannula design, which may be considered traumatic compared to a single needle electrode design.

SUMMARY OF THE INVENTION

In accordance with a first aspect of the invention, a medical probe assembly for ablating tissue is provided. The probe assembly comprises an elongated shaft, which in the preferred embodiment, is sufficiently rigid for percutaneous or laparoscopic introduction into a patient's body. Alternatively, the probe shaft can be flexible, e.g., if the ablation probe takes the form of an intravascular or extravascular catheter. The probe assembly may optionally comprises a cannula with a lumen in which the shaft is reciprocatably disposed in. The probe assembly further comprises an electrode array mechanically coupled to the distal of the shaft. The electrode array comprises a plurality of needle electrodes, at least one of which is configured to assume an outwardly curved shape when exposed to a first temperature. For example, the needle electrode(s) can be composed of a temperature sensitive material, such as Nitinol or a bimetallic metal. The first temperature is preferably greater than body temperature, e.g., equal to the temperature required to ablate tissue.

In the preferred embodiment, the needle electrode(s) is also configured to assume a substantially straight shape when exposed to a second temperature that is less than the first temperature. Preferably, the second temperature is less than the tissue ablation temperature, e.g., body temperature. The electrode array can be deployed within the tissue. For example, the shaft may simply be advanced, such that the electrode array, while exposed to the first temperature, penetrates through the tissue in an outwardly curved fashion. Or the medical probe assembly may optionally comprise a deployment member (e.g., a spring) mechanically coupled between the needle electrode array and the shaft. The deployment member is configured to linearly expand when exposed to a third temperature, which may be the same or different than the first temperature, but is preferably greater than body temperature. For example, the deployment member can be a temperature sensitive material, such as Nitinol.

In accordance with a second aspect of the invention, another medical probe assembly for ablating tissue is provided. The probe assembly comprises an elongated shaft, which may be rigid or flexible as previously described, and an electrode array mechanically coupled to the distal end of the shaft. The electrode array is configured to assume an outwardly curved shape, and preferably a proximally everted shape, when exposed to a first temperature, and assume a pointed tip when exposed to a second temperature less than the first temperature. The first temperature is preferably greater than body temperature, e.g., equal to the tissue ablation temperature, and the second temperature is preferably less than a tissue ablation temperature, e.g., body temperature. In this manner, the pointed tip assumed by the electrode array facilitates introduction of the probe assembly through the tissue prior to the ablation process, while the outwardly curved shape assumed by the electrode array facilitates deployment of the electrode array within the tissue during the ablation process. The exposed needle electrodes also facilitate the visualization of the probe assembly under fluoroscopy. The probe assembly comprises an optional deployment member mechanically coupled between the electrode array and the shaft. The structure and functionality of the deployment member can be similar to that previously described. The probe assembly comprises an optional cannula having a lumen in which the shaft is reciprocatably disposed. In this case, the electrode array may be at least partially retracted into the cannula by displacing the shaft relative to the cannula in a proximal direction. This may be beneficial, e.g., when it is desired to move the probe assembly to a different tissue region for subsequent ablation.

In accordance with a third aspect of the invention, a method of treating tissue having a diseased region, e.g., a tumor, is provided. The method comprises forming a needle electrode array into a single pointed tip in response to a first temperature, e.g., body temperature. The method further comprises forming the electrode array into an outwardly curved array in response to a second temperature that is greater than the first temperature. Preferably, the electrode array is distally displaced through the tissue in order to facilitate the placement of the electrode array into an outwardly curved array, and preferably, a proximally everted array. Displacement of the electrode array through the tissue can be accomplished in response to a third temperature (e.g., by using an expandable member that linearly expands in response to the third temperature), which may be the same as the second temperature. Lastly, the method comprises conveying ablation energy to the electrode array. The ablation energy conveyed through the electrode array may conveniently produce the second temperature. The electrode array can be formed into a single pointed tip again in response to the first temperature, and then introduced into another portion of the diseased region.

BRIEF DESCRIPTION OF THE DRAWINGS

The drawings illustrate the design and utility of preferred embodiments of the present invention, in which similar elements are referred to by common reference numerals, and in which.

DETAILED DESCRIPTION OF THE ILLUSTRATED EMBODIMENTS

Figure 1:
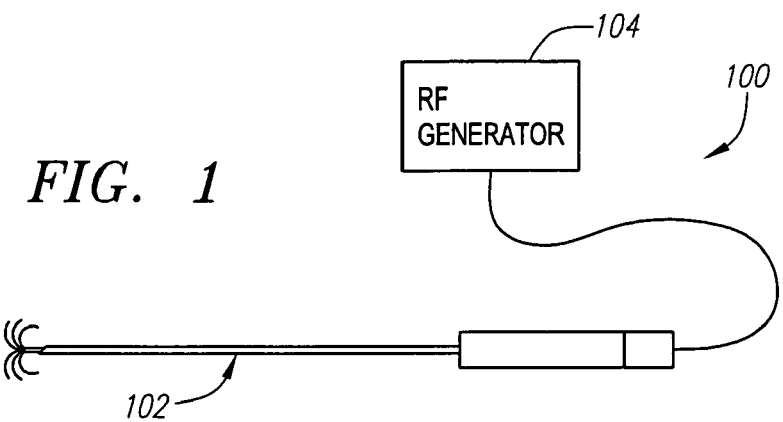
FIG. 1 is a plan view of a tissue ablation system constructed in accordance with one embodiment.
Figure 2:
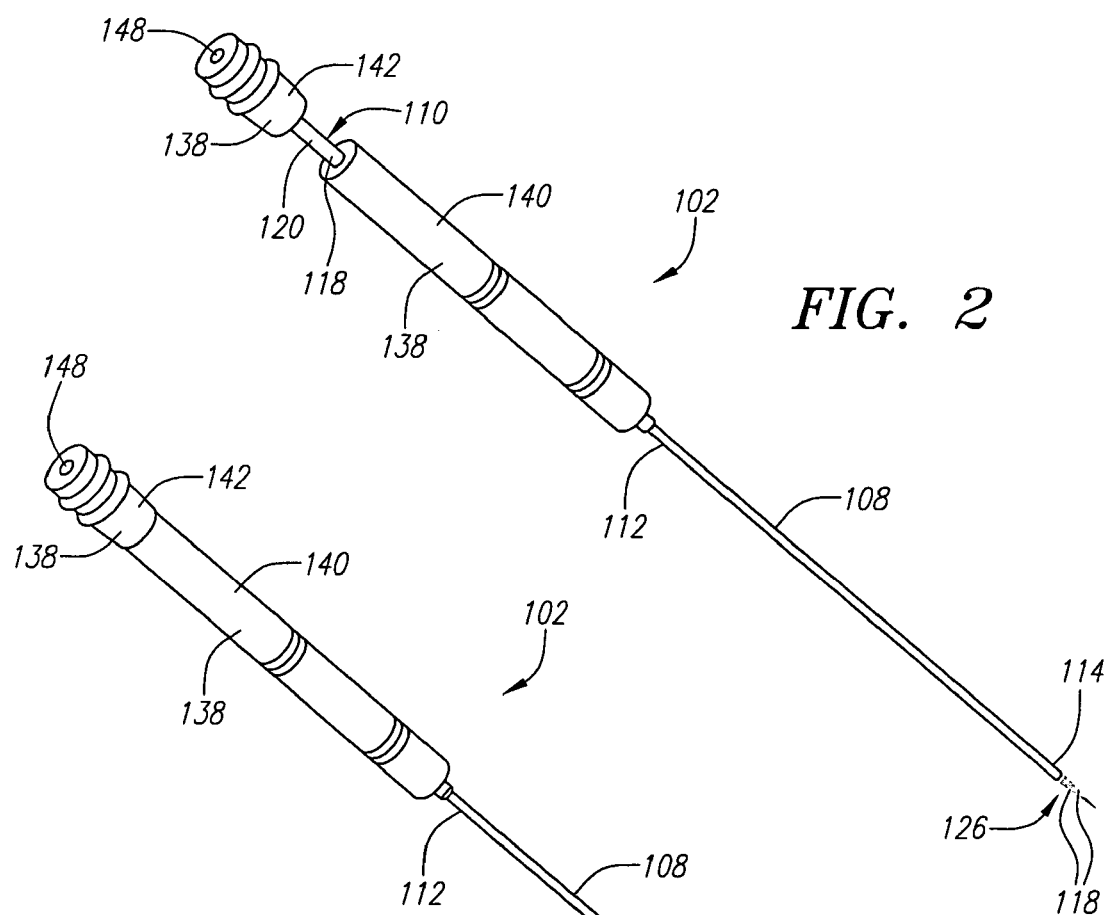
FIG. 2 is a perspective view of an electrode probe assembly that can be used in the tissue treatment system of FIG. 1, wherein a needle electrode array is formed into a pointed tip.

FIG. 1 illustrates a tissue ablation system 100 constructed in accordance with an exemplary embodiment of the invention. The tissue ablation system 100 generally comprises a probe assembly 102 configured for introduction into the body of a patient for ablative treatment of target tissue, and a radio frequency (RF) generator 104 configured for supplying RF energy to the probe assembly 102 in a controlled manner.

Referring specifically now to FIGS. 2–6, the probe assembly 102 generally comprises an elongated cannula 108 and an inner probe 110 slidably disposed within the cannula 108.

As will be described in further detail below, the cannula 108 serves to deliver the active portion of the inner probe 110 to the target tissue. The cannula 108 has a proximal end 112, a distal end 114, and a central lumen 116 extending through the cannula 108 between the proximal end 112 and the distal end 114. As will be described in further detail below, the cannula 108 may be rigid, semi-rigid, or flexible depending upon the designed means for introducing the cannula 108 to the target tissue. The cannula 108 is composed of a suitable material, such as plastic, metal or the like, and has a suitable length, typically in the range from 5 cm to 30 cm, preferably from 10 cm to 20 cm. If composed of an electrically conductive material, the cannula 108 is preferably covered with an insulative material. The cannula 108 has an outside diameter consistent with its intended use, typically being from 1 mm to 5 mm, usually from 1.3 mm to 4 mm. The cannula 108 has an inner diameter in the range from 0.7 mm to 4 mm, preferably from 1 mm to 3.5 mm.

The inner probe 110 comprises a reciprocating shaft 118 having a proximal end 120 and a distal end 122, a cylindrical block 124, an array 126 of tissue penetrating needle electrodes 128 mounted within the cylindrical block 124, and a linearly expanding member 130 mounted between the cylindrical block 124 and the distal shaft end 122. The probe shaft 118 and cylindrical block 124 are preferably composed of an electrically conductive material, such as, e.g., stainless steel. As will be described in further detail below, the electrode array 124 and the expandable member 130 are composed of an electrically conductive temperature sensitive material.

Each of the individual needle electrodes 128 is in the form of a small diameter metal element, which can penetrate into tissue as it is advanced from a target site within the target region. The wires may have circular or non-circular cross-sections, but preferably have rectilinear cross-sections. In this manner, the needle electrodes 128 are generally stiffer in the transverse direction and more flexible in the radial direction. By increasing transverse stiffness, proper circumferential alignment of the needle electrodes 128 within the cannula 108 is enhanced. Exemplary needle electrodes will have a width (in the circumferential direction) in the range from 0.2 mm to 0.6 mm, preferably from 0.35 mm to 0.40 mm, and a thickness (in the radial direction) in the range from 0.05 mm to 0.3 mm, preferably from 0.1 mm to 0.2 mm.

The distal ends of the needle electrodes 128 may be honed or sharpened to facilitate their ability to penetrate tissue. The distal ends of these needle electrodes 128 may be hardened using conventional heat treatment or other metallurgical processes. They may be partially covered with insulation, although they will be at least partially free from insulation over their distal portions. The proximal ends of the needle electrodes 128 are indirectly electrically coupled to the connector assembly (described below) via the expandable member 130 and probe shaft 118.

Figure 5:
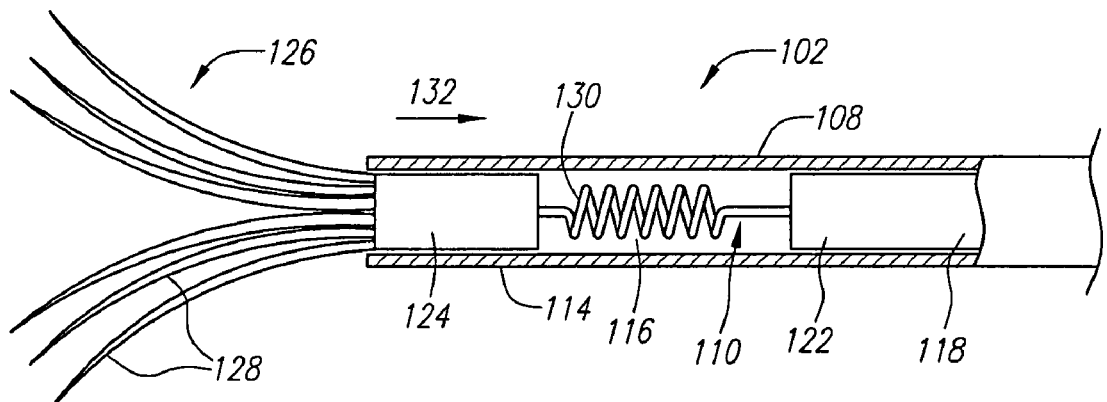
FIG. 5 is a partially cutaway cross-sectional view of the distal end of the probe assembly of FIG. 2, wherein the needle electrode array assumes an outwardly curved shape.
Figure 6:
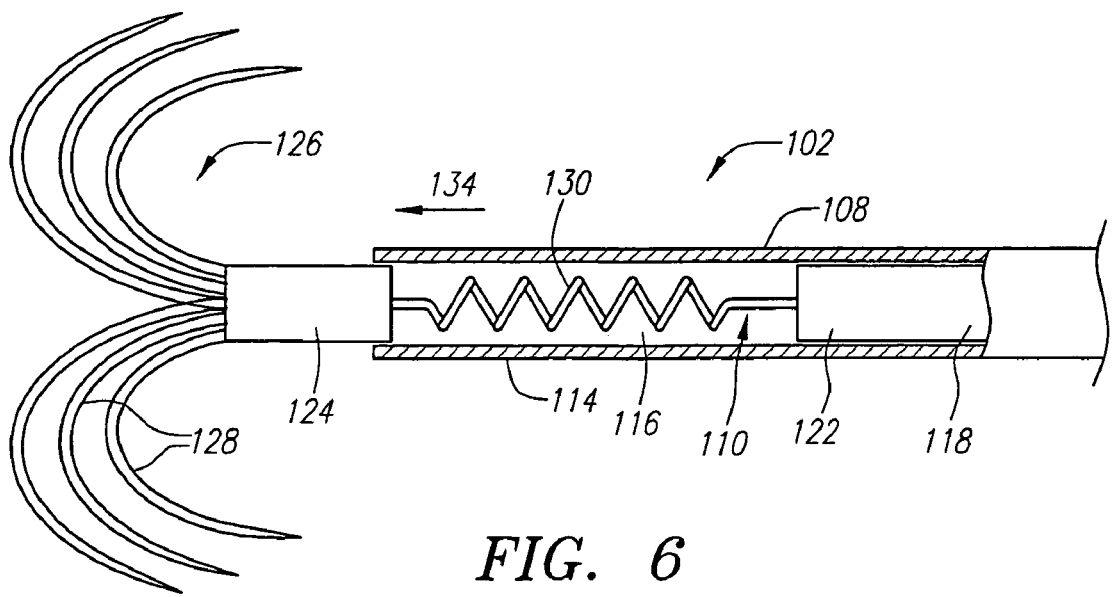
FIG. 6 is a partially cutaway cross-sectional view of the distal end of the probe assembly of FIG. 2, wherein the needle electrode array assumes a proximally everted shape.

It can be appreciated that longitudinal translation of the cylindrical block 124 relative to the cannula 108 in a proximal direction 132 retracts the needle electrode array 126 (FIGS. 4 and 5), while longitudinal translation of the cylindrical block 124 relative to the cannula 108 in a distal direction 134 deploys the electrode array 126 (FIG. 6).

Figure 4:
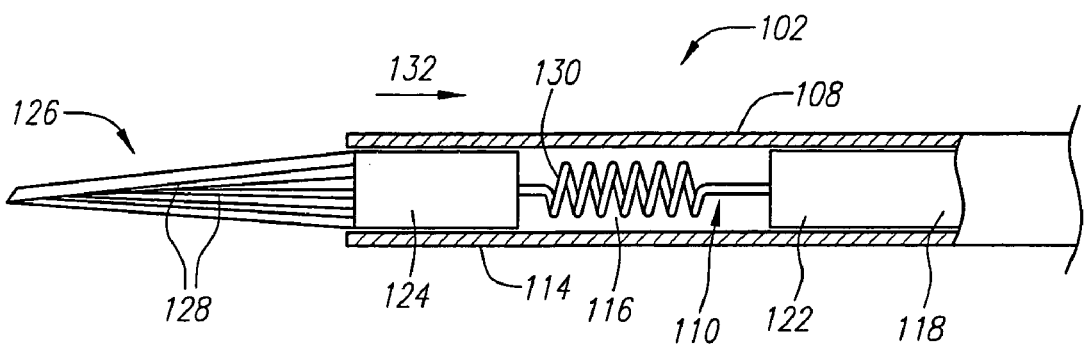
FIG. 4 is a partially cutaway cross-sectional view of the distal end of the probe assembly of FIG. 2, wherein the needle electrode array is formed into a pointed tip.

As illustrated in FIG. 4, the electrode array 126 is configured to be collapsed to form a pointed tip 136 that is capable of penetrating tissue. A smooth transition is provided between the pointed tip 136 and the distal end 114 of the cannula 108, such that tissue trauma that may otherwise be caused by the open distal end 114 of the cannula 108 is minimized. The combination of the needle electrodes 128 advantageously provides the pointed tip 136 with an irregular surface that is more easily viewed under fluoroscopy.

As illustrated in FIGS. 5 and 6, the electrode array 126 is also configured to be expanded to form a three-dimensional shape that usually defines a generally ellipsoidal or spherical volume having a periphery with a maximum radius in the range from 0.5 to 3 cm. In the illustrated embodiment, the needle electrodes 128 diverge radially outwardly from the cannula 108 in a uniform pattern (FIG. 5), i.e., with the spacing between adjacent needle electrodes 128 diverging in a substantially uniform and/or symmetric pattern. In the illustrated embodiment, the needle electrodes 128 also evert proximally (FIG. 6), so that they face partially or fully in the proximal direction 134 when fully deployed. In exemplary embodiments, pairs of adjacent needle electrodes 128 can be spaced from each other in similar or identical, repeated patterns and can be symmetrically positioned about an axis of the probe shaft 118. It will be appreciated that a wide variety of particular patterns can be provided to uniformly cover the region to be treated. It should be noted that a total of six needle electrodes 128 are illustrated in FIG. 1. Additional needle electrodes 128 can be added in the spaces between the illustrated electrodes 128, with the maximum number of needle electrodes 128 determined by the electrode width and total circumferential distance available (i.e., the needle electrodes 128 could be tightly packed).

Figure 3:
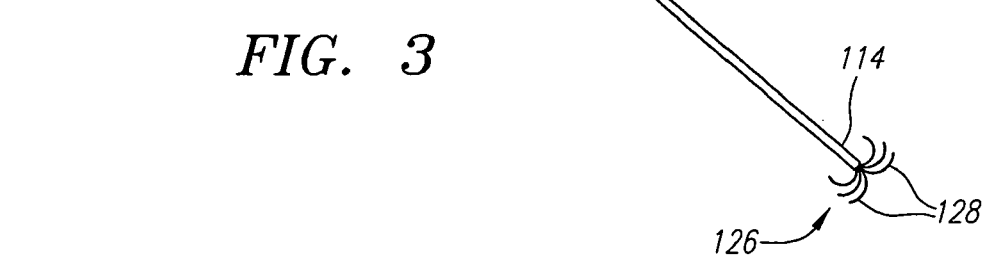
FIG. 3 is a perspective view of the probe assembly of FIG. 2, wherein the needle electrode array is formed in a three-dimensional configuration.

The needle electrodes 128 are resilient and pre-shaped to assume the desired linear configuration (FIGS. 2 and 4) during a given period of time and the desired three-dimensional configuration during another given period of time (FIGS. 3, 5, and 6). Specifically, the needle electrodes 128 are temperature sensitive in that they are composed of a Nitinol material that forms the electrode array 126 into the pointed tip 136 (in the illustrated embodiment, the needle electrodes 128 are substantially rectilinear) when exposed to a relatively low temperature (preferably, below the body temperature, e.g., at room temperature), and forms the electrode array 126 into the three-dimensional configuration when exposed to a relatively high temperature (preferably, tissue ablation temperatures).

Figure 7:
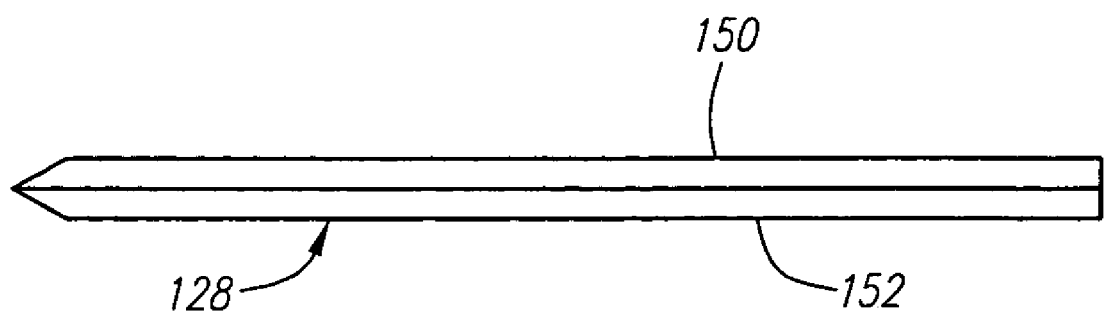
FIG. 7 is a side view of an alternative embodiment of a needle electrode used in the probe assembly of FIG. 3, wherein the needle electrode assumes a rectilinear shape.
Figure 8:
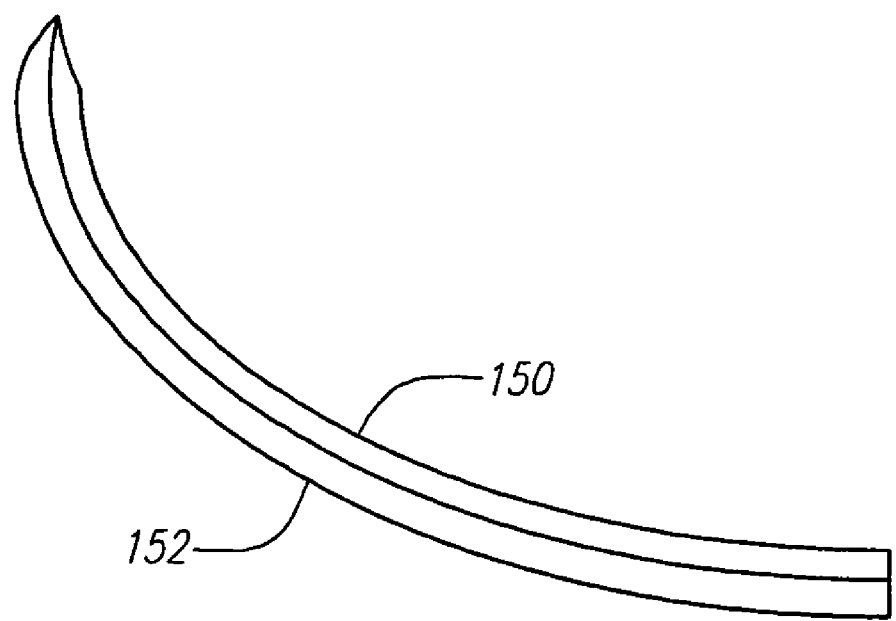
FIG. 8 is a side view of the needle electrode of FIG. 7, wherein the needle electrode assumes an outwardly curved shape.

Alternatively, the needle electrodes 128 can be composed of a bimetallic material, as illustrated in FIGS. 7 and 8. Specifically, each needle electrode 128 comprises an outer layer of metal 150 having a specific coefficient of thermal expansion (CTE) and an inner layer of metal 152 having a higher CTE. For example, the outer layer 150 can be composed of gold, which has a CTE of $7.9 \times 10^{-6}/°$ F. and the inner layer 152 can be composed of copper, which has a CTE of $9.2 \times 10^{-6}/°$ F.

Thus, when the temperature to which the needle electrode 128 is exposed increases above the temperature at which the needle electrode 128 is straight (e.g., from room temperature to ablation temperature), the inner layer 152 will expand along the length of the needle electrode 128 at a rate that is greater than the rate that the outer layer 150 expands along the length of the needle electrode 128. As a result, each needle electrode 128 will deform outward to form the three-dimensional electrode array 126. In contrast, when the temperature to which the needle electrode 128 is exposed decreases below the temperature at which the needle electrode 128 is curved outward (e.g., from ablation temperature back down to body temperature), the inner layer 152 will contract along the length of the needle electrode 128 at a rate that is greater than the rate that the outer layer 150 contracts along the length of the needle electrode 128. As a result, each needle electrode 128 will revert back to being rectilinear to form the pointed tip 136.

Returning to FIGS. 4–6, the linearly expanding member 130 provides the ablation probe 110 with an automated deployment mechanism for the electrode array 126. Specifically, the expanding member 130 is temperature sensitive in that, like the needle electrodes 128, it is composed of a Nitinol material. The expandable member 130 is linearly compressed when exposed to a relatively low temperature (preferably, below the body temperature, e.g., at room temperature), which in turn, maintains the electrode array 126 in its retracted state. In contrast, the expandable member 130 is linearly expanded when exposed to a relatively high temperature (preferably, greater than body temperature), which in turn, deploys the electrode array 126.

Referring back to FIGS. 1 and 2, the probe assembly 102 further comprises a connector assembly 138, which includes a connector sleeve 140 mounted to the proximal end 112 of the cannula 108 and a connector member 142 slidably engaged with the sleeve 140 and mounted to the proximal end 120 of the probe shaft 118. The connector member 142 also comprises an electrical connector 148 to which the probe shaft 118 is electrically coupled. The connector assembly 138 can be composed of any suitable rigid material, such as, e.g., metal, plastic, or the like.

Further details regarding the general structure of needle electrode array-type probe arrangements are disclosed in U.S. Pat. No. 6,379,353, which is hereby expressly incorporated herein by reference.

In the illustrated embodiment, the RF current is delivered to the electrode array 126 in a monopolar fashion, which means that current will pass from the electrode array 126, which is configured to concentrate the energy flux in order to have an injurious effect on the surrounding tissue, and a dispersive electrode (not shown), which is located remotely from the electrode array 126 and has a sufficiently large area (typically 130 cm$^2$ for an adult), so that the current density is low and non-injurious to surrounding tissue. In the illustrated embodiment, the dispersive electrode may be attached externally to the patient, e.g., using a contact pad placed on the patient's flank. In a monopolar arrangement, the needle electrodes 128 are bundled together with their proximal portions having only a single layer of insulation over the cannula 108.

Alternatively, the RF current is delivered to the electrode array 126 in a bipolar fashion, which means that current will pass between "positive" and "negative" electrodes 128 within the array 126. In a bipolar arrangement, the positive and negative needle electrodes 128 will be insulated from each other in any regions where they would or could be in contact with each other during the power delivery phase.

Referring back to FIG. 1, the RF generator 104 is electrically connected to the electrical connector 148 of the connector assembly 138, which as previously described, is directly or indirectly electrically coupled to the electrode array 126. The RF generator 104 is a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200

W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000™ (100 W) and RF3000™ (200 W).

Having described the structure of the tissue ablation system 100, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$ The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 9A:
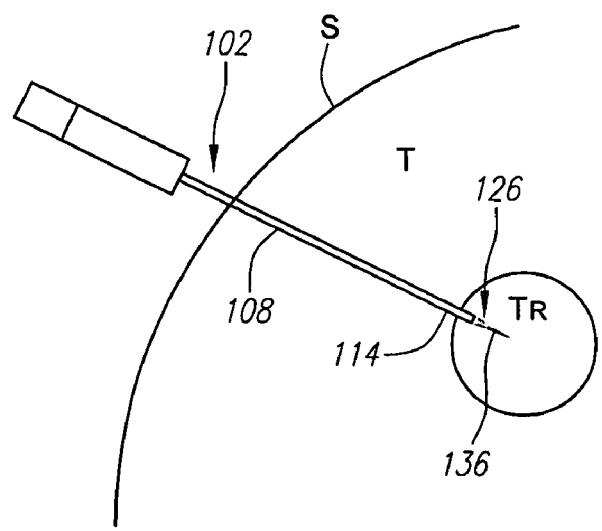
FIGS. 9A–9C illustrates cross-sectional views of one method of using the tissue ablation system of FIG. 1 to treat tissue.
Figure 9B:
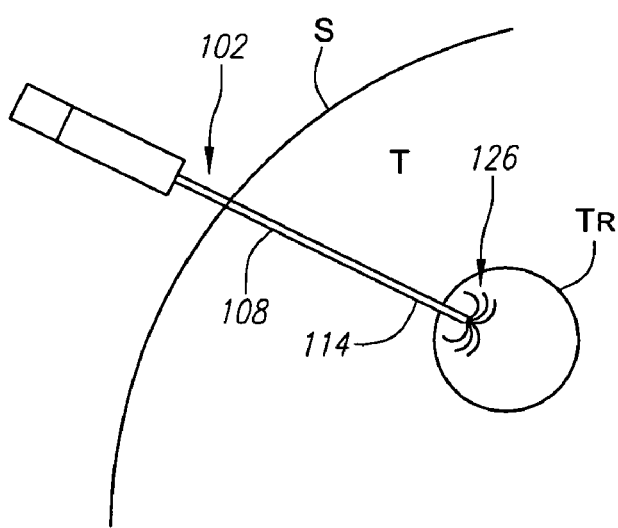
Figure 9C:
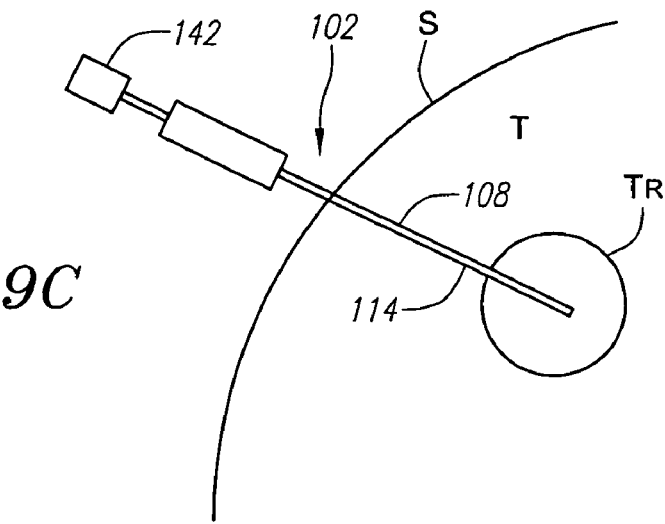

Referring now to FIGS. 9A–9C, the operation of the tissue ablation system 100 is described in treating a treatment region TR within tissue T located beneath the skin or an organ surface S of a patient. The probe assembly 102 is first introduced within the treatment region TR, so that the collapsed needle electrode array 126, i.e., the pointed tip 136 of the ablation probe 110 (not shown in FIGS. 9A–9C) is located within the treatment region TR, as shown in FIG. 9A. Notably, because the needle electrodes 128 are only exposed to body temperature at this time, they will assume their straight configuration, thereby forming the pointed tip 136 to facilitate introduction of the probe assembly 102 through the tissue.

Introduction of the probe assembly 102 into the tissue T can be accomplished using any one of a variety of techniques. In some cases, the probe assembly 102 may be introduced to the target site TS percutaneously directly through the patient's skin or through an open surgical incision. In this case, the pointed tip 136 will facilitate introduction to the treatment region TR. In such cases, it is desirable that the cannula 108 be sufficiently rigid, i.e., have a sufficient column strength, so that it can be accurately advanced through tissue T. In other cases, the cannula 108 may be introduced using an internal stylet that is subsequently exchanged for the probe shaft 118 and electrode array 126. In this latter case, the cannula 108 can be relatively flexible, since the initial column strength will be provided by the stylet. More alternatively, a component or element may be provided for introducing the cannula 108 to the target site TS. For example, a conventional sheath and sharpened obturator (stylet) assembly can be used to initially access the tissue T. The assembly can be positioned under fluoroscopic imaging, with the obturator/stylet then removed to leave an access lumen through the sheath. The cannula 108 and inner probe 110 can then be introduced through the sheath lumen, so that the distal end 114 of the cannula 108 advances from the sheath into the target site TS.

After the electrode array 126 is properly placed, the RF generator 104 is connected to the connector assembly 138 via the electrical connector 148, and then operated to commence the ablation process. As electrical current is conveyed through the expandable member 130 and electrode array 126, the expandable member 130 linearly expands in the distal direction, and the electrode array 126 is transformed from its straight configuration to its three-dimensional configuration. That is, as electrical current passes through the needle electrodes 128, heat is generated, which exposes the electrode array 126 to a temperature that causes needle electrodes 128 to outwardly curve (as shown in FIG. 5). In a practical scenario, however, the lateral movement of the needle electrodes 128 will be hindered by the tissue T. Thus, although the needle electrodes 128 will tend to curve outward, the needle electrodes 128 will not actually curve outward absent distal movement. To this end, as the electrical current passes through the expandable member 130, heat is generated, which exposes the expandable member 130 to a temperature that causes the expandable member 130 to linearly expand, thereby displacing the electrode array 126 in the distal direction. As a result, the electrode array 126 will curve radially outward as it is distally displaced, until the electrode array 126 is proximally everted, as shown in FIG. 9B. The RF generator 104 continues to convey ablation energy to the electrode array 126 until the treatment region TR has been ablated.

If another ablation is required, the connector member 142 may be pulled in the proximal direction relative to the cannula 108 in order to fully retract the electrode array 126 within the cannula 108, as illustrated in FIG. 9C. The expandable member 130 is then placed into its contracted position, and the electrode array 126 is placed in its rectilinear configuration. This can be accomplished by simply waiting for the temperature to which the expandable member 130 and electrode array 126 is exposed to drop, or by dipping the probe assembly 102 into a chilled solution. Once the expandable member 130 is fully contracted and the needle electrodes 128 are placed into their rectilinear configuration, the connector member 142 can then be pushed in the distal direction relative to the cannula 108 in order to move the pointed tip 136 formed by the electrode array 126 out of the distal end 114 of the cannula 108. The probe assembly 102 can then be repositioned within the treatment region TR and operated again to create another lesion.

Although particular embodiments of the invention have been shown and described herein, there is no intention to the present invention to the disclosed embodiments. Indeed, and it will be apparent to those skilled in the art that various changes and modifications may be made without departing from the scope of the invention, as recited in the following claims.

What is claimed is:

1. A medical probe assembly for ablating tissue comprising:
   an elongated shaft having a deployment member configured to linearly expand in response to being exposed to a first temperature;
   an electrode array comprising a plurality of needle electrodes, the electrode array mechanically coupled to the deployment member, wherein the electrode array is configured to be axially displaced in a distal direction when the deployment member linearly expands, and wherein the electrode array is configured to assume an outwardly curved shape in response to being exposed to a second temperature, and narrow to a single pointed tip in response to being exposed to a third temperature less than the second temperature.

2. The medical probe assembly of claim 1, wherein the second temperature equals the first temperature.

3. The medical probe assembly of claim 1, wherein each of the needle electrodes comprises Nitinol.

4. The medical probe assembly of claim 1, wherein each or the needle electrodes is bi-metallic.

5. The medical probe assembly of claim 1, wherein the first temperature is greater than body temperature.

6. The medical probe assembly of claim 1, wherein the first temperature is equal to a tissue ablation temperature.

7. The medical probe assembly of claim 1, wherein each of the needle electrodes is configured to assume a substantially straight shape in response to being exposed to the third temperature.

8. The medical probe assembly of claim 1, wherein the third temperature is body temperature.

9. The medical probe assembly of claim 1, wherein the deployment member is mechanically coupled between the electrode array and the shaft.

10. The medical probe assembly of claim 1, wherein the deployment member comprises Nitinol.

11. The medical probe assembly of claim 1, wherein the deployment member comprises a spring.

12. The medical probe assembly of claim 1, further comprising a cannula having a lumen, wherein the shaft is reciprocatably disposed within the cannula lumen.

13. A medical probe assembly for ablating tissue, comprising:
    an elongated shaft having a proximal end and a distal end; and
    an electrode array mechanically coupled to the distal end of the shaft, the electrode array configured to assume an outwardly curved shape in response to being exposed to a first temperature, and narrow to a single pointed tip in response to being exposed to a second temperature less than the first temperature.

14. The medical probe assembly of claim 13, wherein the elongated shaft is rigid.

15. The medical probe assembly of claim 13, wherein the electrode array is configured to proximally evert when exposed to the first temperature.

16. The medical probe assembly of claim 13, wherein the electrode array comprises Nitinol.

17. The medical probe assembly of claim 13, wherein the electrode array is bi-metallic.

18. The medical probe assembly of claim 13, wherein the first temperature is equal to a tissue ablation temperature, and the second temperature is equal to body temperature.

19. The medical probe assembly of claim 13, further comprising a deployment member mechanically coupled between the electrode array and the shaft, the deployment member configured to linearly expand in response to being exposed to a third temperature that is greater than the second temperature.

20. The medical probe assembly of claim 19, wherein the third temperature is the same as the first temperature.

21. The medical probe assembly of claim 19, wherein the third temperature is different from the first temperature.

22. The medical probe assembly of claim 19, wherein the deployment member comprises Nitinol.

23. The medical probe assembly of claim 19, wherein the deployment member comprises a spring.

24. The medical probe assembly of claim 13, further comprising a cannula having a lumen, wherein the shaft is reciprocatably disposed within the cannula lumen.

25. The medical probe assembly of claim 24, wherein the electrode array is configured to be at least partially retracted into the cannula by displacing the shaft relative to the cannula in a proximal direction.

26. A method of treating tissue having a diseased region with a needle electrode array initially formed into a single pointed tip in response to a first temperature, comprising:
    introducing the single pointed tip into the tissue adjacent the diseased region, wherein the single pointed tip is used to penetrate the tissue;
    forming the electrode array into an outwardly curved array in response to a second temperature greater than the first temperature; and
    conveying ablation energy to the electrode array to ablate the diseased region.

27. The method of claim 26, wherein the ablation energy produces the second temperature.

28. The method of claim 26, wherein the electrode array is formed into the outwardly curved array further in response to the displacement of the electrode array through the diseased region.

29. The method of claim 26, wherein the electrode array is displaced through the diseased region in response to a third temperature.

30. The method of claim 29, wherein the third temperature is the same as the second temperature.

31. The method of claim 29, wherein the third temperature is different from the second temperature.

32. The method of claim 26, further comprising forming the electrode array into a proximally everted array in response to the second temperature.

33. The method of claim 26, further comprising forming the needle electrode array into the single pointed tip again in response to the first temperature, and introducing the single pointed tip into another portion of the tissue.

34. The method of claim 26, wherein the diseased region is a tumor.

* * * * *